United States Patent [19]

Takahashi et al.

[11] Patent Number: 5,015,282

[45] Date of Patent: May 14, 1991

[54] FRESHNESS PRESERVING AGENT

[75] Inventors: Nobumitsu Takahashi, Yokohama; Kenichi Yoshie, Machida, both of Japan

[73] Assignee: Mitsubishi Kasei Corporation, Tokyo, Japan

[21] Appl. No.: 388,517

[22] Filed: Aug. 2, 1989

[30] Foreign Application Priority Data

Aug. 10, 1988 [JP] Japan ................... 63-199167

[51] Int. Cl.$^5$ .................. A01N 3/02; A23B 7/153
[52] U.S. Cl. ........................... 71/65; 71/68; 426/270; 426/331; 426/333; 426/419
[58] Field of Search .............. 71/65, 68; 426/270, 426/331, 333, 419

[56] References Cited

U.S. PATENT DOCUMENTS

| 4,000,246 | 12/1976 | Walles | 423/230 |
| 4,234,460 | 11/1980 | Nishimura et al. | 252/447 |
| 4,256,773 | 3/1981 | Itoga et al. | 426/415 |
| 4,260,750 | 4/1981 | Kuntz | 544/178 |

FOREIGN PATENT DOCUMENTS

| 10776 | 6/1981 | Japan . |
| 63048 | 4/1982 | Japan . |
| 25340 | 6/1986 | Japan . |

Primary Examiner—Allen J. Robinson
Assistant Examiner—Brian Bembenick
Attorney, Agent, or Firm—Oblon, Spivak, McClelland, Maier & Neustadt

[57] ABSTRACT

A freshness preserving agent comprising carbon black having a specific surface area of at most 1,000 m$^2$/g as measured by BET method and a palladium compound supported thereon.

10 Claims, No Drawings

FRESHNESS PRESERVING AGENT

BACKGROUND OF THE INVENTION

1. Field of the Invention

The present invention relates to freshness preserving agent for e.g. flowers, vegetables and fruits.

2. Discussion of Background

Heretofore, ethylene has been known as a modified gas component generated from vegetables and fruits. The amount of ethylene generated from plant bodies is extremely large, and in the case of climacteric fruits, the amount is said to reach 10 ml/kg/day. On the other hand, the threshold value of ethylene which induces a physiological change is extremely small at a level of from 0.1 to 3 ppm.

As a freshness preserving agent which removes such ethylene as the modified gas component, active carbon, potassium permanganate, bromine-absorbed carbon or active carbon having palladium chloride supported thereon, has been, for instance, known.

However, with active carbon, the ethylene absorptivity at a low ethylene concentration is low, and the effect as a freshness preserving agent is still inadequate. Potassium permanganate contains heavy metals, and its use for food products is very dangerous and improper because of the toxicity and the explosive nature. Bromine-absorbed carbon (U.S. Pat. No. 4,256,773) is not suitable for food products, since bromine and ethylene react to each other to form ethylene dibromide which has a carcinogenic nature. In the case of active carbon having palladium chloride supported thereon (Japanese Examined Patent Publication No. 25340/1986), there is no problem of toxicity, but the speed for the removal of ethylene is slow, and the amount of ethylene thereby treated is small, and the effect is inadequate in that it is impossible to completely remove ethylene to a low concentration.

SUMMARY OF THE INVENTION

It is an object of the present invention to provide a highly effective freshness preserving agent which has a particularly high absorption rate and treating amount for ethylene gas and which is capable of completely removing ethylene to a low ethylene concentration.

The present invention provides a freshness preserving agent comprising carbon black having a specific surface area of at most 1,000 $m^2/g$ as measured by BET method and a palladium compound supported thereon.

DETAILED DESCRIPTION OF THE PREFERRED EMBODIMENT

Now, the present invention will be described in detail with reference to the preferred embodiments.

In the freshness preserving agent of the present invention, carbon black having a specific surface area of at most 1,000 $m^2/g$ as measured by BET method is used as a carrier. Carbon black is particles obtained by thermally decomposing a gaseous or liquid hydrocarbon or heavy oil, wherein fine crystals having a random layered structure formed by a plurality of layers of flat aromatic molecules, are aggregated in a complicated fashion to form certain primary particles of amorphous carbon, and such primary particles are linearly connected to form a construction called a structure. There is no particular restriction as to the method for the preparation of carbon black. The carbon black may be oil furnace black produced by a conventional furnace process, lamp black produced by a lamp process, thermal black produced by a thermal process, acetylene black produced by decomposition of acetylene, roller black, disk black and byproduct carbon black from heavy oil decomposition process. Any one of these materials may be used as the carbon black for the present invention. The carbon black to be used in the present invention is required to have a specific surface area of at most 1,000 $m^2/g$ as measured by BET method (see "Carbon Black" Jean-Baptiste Donnet, Andries Voet, Marcel Dekker, Inc., New York and Basel 1976, 58–63). The specific surface area is preferably from 100 to 800 $m^2/g$, more preferably from 150 to 500 $m^2/g$, most preferably from 200 to 450 $m^2/g$. Further, the dibutyl phthalate (DBP) oil absorption as another physical property of the carbon black is usually from 50 to 400 ml/100 g, preferably from 100 to 300 ml/100 g, most preferably from 150 to 250 ml/100 g.

Furthermore, the primary particle size is usually from 10 to 300 m$\mu$m, preferably from 15 to 80 m$\mu$m, most preferably from 20 to 40 m$\mu$m.

The surface pH of the carbon black is preferably at least 6.

The carbon black to be used in the present invention may be the one subjected to degassing treatment. The degassing treatment is usually conducted by heating under reduced pressure at a temperature of from 700 to 1,300° C. in one hour. By the degassing treatment, functional groups on the surface of the carbon black, such as carboxyl groups or carbonyl groups will be removed, whereby the surface pH of the carbon black tends to be high.

The freshness preserving agent of the present invention is characterized by using the above-mentioned carbon black as a carrier and supporting a palladium compound thereon. As the palladium compound, palladium chloride, palladium bromide, palladium nitrate, palladium sulfate and palladium acetate may, for example, be mentioned. Particularly preferred is palladium chloride. The amount of the palladium compound supported is usually from 0.05 to 10% by weight, preferably from 0.1 to 5% by weight, based on the total amount of the carbon black and the palladium compound. If the amount supported is small, no adequate ethylene removing effect is obtainable. On the other hand, if the amount is too much, no additional effect will be obtained, whereby the efficiency tends to decrease. As a method of supporting a palladium compound to carbon black, carbon black is put into an aqueous solution of a mineral acid having a concentration of from 0.1 to 5N, such as an aqueous solution of hydrochloric acid, nitric acid or sulfuric acid, containing a palladium compound, followed by stirring to let the palladium compound adsorbed, followed by filtration and drying at a temperature of from 110° to 300° C., to obtain a palladium compound-supporting carbon black.

When the palladium compound-supporting carbon black thus obtained is used as a freshness preserving agent, a large amount of ethylene can be treated quickly at a low temperature around the room temperature, and it is thereby possible to bring the ethylene concentration of the gas phase to 0 in a short period of time.

The freshness preserving agent having a palladium compound supported on the carbon black may be used in combination with other ethylene absorbers, or with other known freshness preserving agents such as active carbon or a porous carrier such as zeolite or alumina, being an absorber for a gas hazardous to fruits such as an aldehyde or an alcohol. The amount of such other freshness preserving agent to be used in combination with the freshness preserving agent of the present invention, is usually from 1 to 100 parts by weight, preferably from 3 to 20 parts by weight, most preferably from 5 to 15 parts by weight, per 1 part by weight of the freshness preserving agent of the present invention i.e. the palladium compound-supporting carbon black. As other freshness preserving agent to be used in combination, active carbon is particularly preferred. By using such other freshness preserving agent in combination, it is possible to reduce the amount of palladium supported in the freshness preserving agent of the present invention, since the initial ethylene absorbing effect can be increased by such combined use.

Now, the manner of using the freshness preserving agent of the present invention will be described.

The freshness preserving agent of the present invention is placed together with flowers, vegetables or fruits in a closed container made of a film or sheet of a plastic material such as polyethylene or polypropylene or in a refrigerator. There is no particular restriction as to the form in which it is placed. For example, it is common to employ a method in which the freshness preserving agent is packed in a gas permeable bag made of e.g. paper, cloth or non-woven fabric and the bag is placed in the closed container, or a method wherein the freshness preserving agent is fixed in the inner wall of the closed container. Further, it may be incorporated in a film of a plastic material such as polyethylene or polypropylene or in a moisture absorptive paper.

The amount of the freshness preserving agent varies depending upon the type and amount of the vegetables and fruits. However, it is usually employed in an amount within a range of from 0.05 to 50 g per kg of the vegetables or fruits.

The freshness preserving agent of the present invention may be used for all flowers, vegetables or fruits. For example, it is useful for fruits such as apples, pears, oranges, bananas, grapes, KABOSU or Japanese apricot, for vegetable fruits such as tomatos, strawberries or green peppers, vegetables such as bamboo shoots, mushrooms, spinages, leeks, lettuces or cabbages, and for flowers such as carnation.

The freshness preserving agent of the present invention having a palladium compound supported on carbon black having a specific surface area of at most 1,000 m$^2$/g, is capable of removing ethylene to a low concentration over a long period of time and exhibits excellent effects as a freshness preserving agent for flowers, vegetables and fruits.

Now, the present invention will be described in further detail with reference to Examples. However, it should be understood that the present invention is by no means restricted to such specific Examples.

EXAMPLE 1

6.66 g of carbon black #3250 (manufactured by Mitsubishi Kasei Corporation, particle size: 28 m$\mu$m, specific surface area: 240 BET-m$^2$/g, DBP oil absorption: 180 ml/100 g) was put into 60 ml of a 1N hydrochloric acid aqueous solution containing 66.6 mg of palladium chloride and immersed for one hour to let the palladium compound be adsorbed. Then, the carbon black was collected by filtration and dried for one hour in a nitrogen stream (330 mlN$_2$/min) of 200° C., to obtain carbon black having a palladium compound supported in an amount of about 1% by weight (Sample No. 1). The amount of the palladium compound supported, was calculated from the amount of palladium remaining in the residual solution after filtration.

In the same manner, active carbon having 1.0% of a palladium compound supported (Sample No. 2) was prepared by using coconut shell active carbon (DIASORB® W, trademark, manufactured by Mitsubishi Kasei Corporation, specific surface area: 1,200 BET-m$^2$/g).

0.9 g of the above-mentioned coconut shell active carbon (DIASORB® W) not treated was added to 0.1 g of the above-mentioned palladium compound-supporting carbon black (Sample No. 1), or to 0.1 g of the palladium compound-supporting active carbon (Sample No. 2), respectively (the amount of non-treated active carbon was 0.9 g relative to 1 mg of palladium), to obtain Samples Nos. 3 and 4, respectively.

TEST EXAMPLES 1 to 4 and COMPARATIVE TEST EXAMPLES 1 to 4

With respect to each Sample obtained in Example 1, the ethylene removal ability per 1 mg of palladium was measured in accordance with the following methods.

(1) Measuring method 1

Each sample in an amount corresponding to 1 mg of palladium was put into a glass jar having an internal capacity of 2 l and containing water. One day later, 2 ml of ethylene was injected (initial ethylene concentration of gas phase: 1,000 ppm), and the change with time of the ethylene concentration of gas phase was measured by gas chromatography. The results are shown in Table 1.

(2) Measuring method 2

Each sample in an amount corresponding to 1 mg of palladium was put into a glass jar having an internal capacity of 2 l and containing water. One day later, 1 ml of ethylene was injected (first time) (initial ethylene concentration of gas phase: 500 ppm), and the change with time of the ethylene concentration of gas phase was measured by gas chromatography. 48 Hours after the first ethylene injection, 1 ml of ethylene was further injected (second time), and the change with time of the ethylene concentration of gas phase after the second ethylene injection was measured by gas chromatography. The results are shown in Table 2.

TABLE 1

| | Sample No. | Ethylene absorbing agent | Physical properties of carbon black or active carbon | | Amount used (g) | Ethylene concentration of gas phase (ppm) | | |
|---|---|---|---|---|---|---|---|---|
| | | | Specific surface area (m$^2$/g) | DBP oil absorption (ml/100 g) | | Time passed since the addition of ethylene | | |
| | | | | | | 2 hr | 4 hr | 24 hr |
| Test Example 1 | 1 | PdCl$_2$ 1.0% supporting | 240 | 180 | 0.1 | 720 | 600 | 110 |

TABLE 1-continued

| | Sample No. | Ethylene absorbing agent | Physical properties of carbon black or active carbon | | Amount used (g) | Ethylene concentration of gas phase (ppm) | | |
|---|---|---|---|---|---|---|---|---|
| | | | Specific surface area (m²/g) | DBP oil absorption (ml/100 g) | | Time passed since the addition of ethylene | | |
| | | | | | | 2 hr | 4 hr | 24 hr |
| Comparative Test Example 1 | 2 | carbon black (#3250) PdCl₂ 1.0% supporting active carbon (DIASORB ® W) | 1200 | — | 0.1 | 800 | 690 | 250 |
| Test Example 2 | 3 | PdCl₂ 1.0% supporting carbon black (#3250), Active carbon (DIASORB ® W) | 240 1200 | 180 — | 0.1 0.9 | 630 | 500 | 50 |
| Comparative Test Example 2 | 4 | PdCl₂ 1.0% supporting Active carbon (DIASORB ® W), Active carbon (DIASORB ® W) | 1200 1200 | — — | 0.1 0.9 | 730 | 580 | 180 |

TABLE 2

| | Sample No. | Ethylene absorbing agent | Amount used (g) | Total amount of added ethylene (ml) | Ethylene concentration of gas phase (ppm) Time passed since the addition of ethylene | | | |
|---|---|---|---|---|---|---|---|---|
| | | | | | 4 hr | 24 hr | 48 hr | 72 hr |
| Test Example 3 | 1 | PdCl₂ 1.0% supporting carbon black (#3250) | 0.1 | 1.0 *2.0 | 215 380 | 8 130 | 0 | 9 |
| Comparative Test Example 3 | 2 | PdCl₂ 1.0% supporting active carbon (DIASORB ® W) | 0.1 | 1.0 *2.0 | 360 470 | 125 260 | 46 | 87 |
| Test Example 4 | 3 | PdCl₂ 1.0% supporting carbon black (#3250), Active carbon (DIASORB ® W) | 0.1 0.9 | 1.0 *2.0 | 190 400 | 4 140 | 0 | 7 |
| Comparative Test Example 4 | 4 | PdCl₂ 1.0% supporting Active carbon (DIASORB ® W), Active carbon (DIASORB ® W) | 0.1 0.9 | 1.0 *2.0 | 320 475 | 90 320 | 33 | 175 |

* 1 ml of ethylene was first injected and 48 hours later, 1 ml of ethylene was further injected.

EXAMPLE 2

By using carbon black or active carbon having the physical properties as identified in Table 3, as the carrier, a palladium compound 0.5 wt. %-supporting or 1 wt. %-supporting carbon black or active carbon was prepared in the same manner as in Example 1.

The carbon black used as the carrier in Test Examples 9 and 10 was the same carbon black as used as the carrier in Test Exaples 5 and 6 except that it was subjected to degassing treatment under a reduced pressure of 0.2 mmHg at 1,100° C. for 30 minutes.

TEST EXAMPLES 5 to 16 and COMPARATIVE TEST EXAMPLES 5 to 7

The ethylene absorption of 0.1 g of each sample obtained in Example 2 (which corresponds to ethylene absorption per 0.5 mg or 1 mg of palladium) was measured in accordance with the following method.

(1) Measuring method 0.1 g of each sample was put into a glass jar having an internal capacity of 2 l and containing water. One day later, 2 ml of ethylene was injected (initial gas phase ethylene concentration: 1,000 ppm), and 24 hours after the injection, the amount of ethylene gas in the gas phase was measured by gas chromatography, and from this value, the ethylene absorption was calculated.

TABLE 3

| | Ethylene absorbing agent | Physical properties of carrier | | | | Ethylene absorption after 24 hours (ml) |
|---|---|---|---|---|---|---|
| | | Specific surface area (m²/g) | DBP oil absorption (ml/100 gCB) | Particle size (m μm) | Surface pH | |
| Test Example 5 | PdCl₂ 0.5% supporting carbon black | 240 | 180 | 28 | 7 | 1.66 |
| Test Example 6 | PdCl₂ 1.0% supporting carbon black | " | " | " | " | 1.93 |
| Test Example 7 | PdCl₂ 0.5% supporting carbon black | 261 | 180 | 28 | 7 | 1.42 |
| Test Example 8 | PdCl₂ 1.0% supporting carbon black | " | " | " | " | 1.93 |
| Test Example 9 | PdCl₂ 0.5% supporting carbon black | 240 | 180 | 28 | 8.5 | 1.84 |
| Test Example 10 | PdCl₂ 1.0% supporting carbon black | " | " | " | " | 1.96 |
| Test Example 11 | PdCl₂ 0.5% supporting carbon black | 443 | 211 | 28 | 8 | 1.30 |
| Test Example 12 | PdCl₂ 1.0% supporting carbon black | " | " | " | " | 1.94 |
| Test Example 13 | PdCl₂ 0.5% supporting carbon black | 343 | 186 | 16 | 7 | 1.25 |

TABLE 3-continued

| | Ethylene absorbing agent | Physical properties of carrier | | | | Ethylene absorption after 24 hours (ml) |
|---|---|---|---|---|---|---|
| | | Specific surface area (m²/g) | DBP oil absorption (ml/100 gCB) | Particle size (m μm) | Surface pH | |
| Test Example 14 | PdCl₂ 1.0% supporting carbon black | " | " | " | " | 1.90 |
| Test Example 15 | PdCl₂ 0.5% supporting carbon black | 964 | 280 | 16 | 7 | 1.03 |
| Test Example 16 | PdCl₂ 1.0% supporting carbon black | " | " | " | " | 1.82 |
| Comparative Test Example 5 | PdCl₂ 0.5% supporting carbon black | 1245 | 321 | 16 | 7 | 0.69 |
| Comparative Test Example 6 | PdCl₂ 0.5% supporting carbon black | 1500 | 360 | 16 | 7 | 0.30 |
| Comparative Test Example 7 | PdCl₂ 0.5% supporting active carbon (DIASORB ® W) | 1200 | — | — | | 0.47 |

What is claimed is:

1. A freshness preserving agent comprising carbon black having a specific surface area of at most 1,000 m²/g as measured by BET method and having a dibutyl phthalate oil absorption of from 100 to 300 ml per 100 g of the carbon black, and a palladium compound supported thereon.

2. The freshness preserving agent according to claim 1, wherein the specific surface area of the carbon black is from 100 to 800 m²/g.

3. The freshness preserving agent according to claim 2, wherein the specific surface area of the carbon black is from 150 to 500 m²/g.

4. The freshness preserving agent according to claim 1, wherein the primary particle size of the carbon black is from 10 to 300 mμm.

5. The freshness preserving agent according to claim 4, wherein the primary particle size of the carbon black is from 15 to 80 mμm.

6. The freshness preserving agent according to claim 1, wherein the amount of the palladium compound supported is from 0.05 to 10% by weight based on the total amount of the palladium compound and the carbon black.

7. The freshness preserving agent according to claim 6, wherein the amount of the palladium compound supported is from 0.1 to 5% by weight.

8. The freshness preserving agent according to claim 1, wherein the palladium compound is palladium chloride.

9. The freshness preserving agent according to claim 1, which further contains active carbon as an additional fresh preserving agent.

10. The freshness preserving agent according to claim 1, wherein the carbon black has a dibutyl phthalate oil absorption of from 100 to 300 ml per 100 g of the carbon black, the primary particle size of the carbon black is from 10 to 300 mμm, the palladium compound is palladium chloride, and the amount of the palladium compound supported is from 0.05 to 10% by weight based on the total amount of the palladium compound and the carbon black.